United States Patent [19]
Klingenbeck et al.

[11] Patent Number: 4,805,627
[45] Date of Patent: Feb. 21, 1989

[54] METHOD AND APPARATUS FOR IDENTIFYING THE DISTRIBUTION OF THE DIELECTRIC CONSTANTS IN AN OBJECT

[75] Inventors: Klaus Klingenbeck, Hessdorf; Judith Regn, Nuremberg, both of Fed. Rep. of Germany

[73] Assignee: Siemens Aktiengesellschaft, Berlin and Munich, Fed. Rep. of Germany

[21] Appl. No.: 903,999

[22] Filed: Sep. 4, 1986

[30] Foreign Application Priority Data

Sep. 6, 1985 [DE] Fed. Rep. of Germany ....... 3531893

[51] Int. Cl.⁴ .............................................. A61B 6/00
[52] U.S. Cl. ............................... 128/653; 324/58.5 A; 73/602
[58] Field of Search ....................... 128/653, 804, 660; 324/58.5 A, 58.5 R; 73/602, 607

[56] References Cited

U.S. PATENT DOCUMENTS

| | | |
|---|---|---|
| 3,562,642 | 2/1971 | Hochschild . |
| 3,818,427 | 6/1974 | Pekau et al. . |
| 3,887,923 | 6/1975 | Hendrix . |
| 4,033,697 | 7/1977 | Pfoutz et al. ......................... 356/386 |
| 4,135,131 | 1/1979 | Larsen et al. ........................ 128/653 |
| 4,234,844 | 11/1980 | Yukl . |
| 4,247,815 | 1/1981 | Larsen et al. ................... 324/58.5 A |
| 4,552,151 | 11/1985 | Bolomey et al. . |
| 4,641,659 | 2/1987 | Sepponen ............................ 128/653 |
| 4,652,755 | 3/1985 | Solomon et al. ..................... 356/346 |
| 4,662,222 | 5/1987 | Johnson ............................... 128/660 |

OTHER PUBLICATIONS

Jacobi et al, "Water Immersed Microwave Antennas and their Application to Microwave Interrugation of Biological Targets", IEEE Transactions on Microwave Theory and Techniques, vol. MTT-27 No. 1 Jan. 1979, pp. 70–78.

Jacobi et al, "Microwave Time Delay Spectroscopic Imagery of Isolated Canine Kidney", Med. Phys vol. 7 No. 1 Jan./Feb. 1980 pp. 1–7.

Burdette et al, "In vivo Probe Measurement Technique for Determining Dielectric Properties at VHF Through Microwave Frequencies", IEEE Transactions of Microwave Theory and Techniques, vol. MTT-28, No. 4 Apr. 1980, pp. 414–427.

"Limitations of Imaging With First-Order Defraction Tomogrpahy," Slaney et al IEEE Trans. On Microwave Theory and Techniques, vol. MTT-32, No. 8, Aug. 1984, pp. 860–874.

"A Microwave Defraction Tomography System for Biomedical Applications," Peronnet et al, Proc. of Thirteenth Microwave Conference, Nuremburg, Germany, Sep. 1983, pp. 529–533.

"Distortion in Defraction Tomography Caused by Multiple Scattering," Azimi et al, IEEE Trans. on Medical Imaging, vol. MI-2, No. 4, Dec. 1983, pp. 176–195.

"3-D Holographic Device Images RF Data Collected Once Over Entire Body," Pearce et al, RNM Images, Apr. 1984, pp. 32–33, 37.

Primary Examiner—Ruth S. Smith

[57] ABSTRACT

A method and apparatus for identifying the distribution of the dielectric constants in an object employ radiation emitted by a microwave transmitter directed at the object, which radiation is received by a microwave detector array. The dielectric constant distribution is calculated in a computer from the output signal of the detector array, and is represented on a monitor. The transmitted and scattered radiation is acquired by the array in a prescribed volume in terms of amplitude and phase. For this purpose, the array has a surface with detector elements thereon which is linearly displaceable in a direction toward the microwave transmitter in steps along a selected path. At each step, the incoming radiation is identified in terms of amplitude and phase at a plurality of measuring locations, the number of measuring locations corresponding to the number of individual detector elements within the array. This measuring phase is thereafter combined with a calibration phase for further processing.

23 Claims, 2 Drawing Sheets

METHOD AND APPARATUS FOR IDENTIFYING THE DISTRIBUTION OF THE DIELECTRIC CONSTANTS IN AN OBJECT

BACKGROUND OF THE INVENTION

1. Field of the Invention

The present invention relates to a method and apparatus for identifying the distribution of dielectric constants in an object employing microwave radiation and providing a visual presentation of the object.

2. Description of the Prior Art

A method for identifying the distribution of dielectric constants in an object is generally described in IEEE Transactions on Medical Imaging, Vol. MI-2, No. 4, December 1983, at pages 176–195. In this method, radiation is emitted by a microwave transmitter and irradiates an object to be examined. Radiation passing through and scattered by the object is measured in terms of amplitude and phase by a microwave detector. The distribution of the dielectric constants in the object is calculated from the output signal of the detector, and is forwarded to a means for visually displaying an image of the object.

Various efforts have been undertaken to provide a satisfactory method for identifying the distribution of dielectric constants $\epsilon$ in biological tissue, particularly in the human body. These efforts are based on the perception that the physical quantity $\epsilon$, critical for the interaction of electromagnetic radiation with biological tissue, can be used for imaging in medical diagnostics.

Early efforts in diffraction tomography have used either stationary linear antenna arrays, as described in "Limitations of Imaging With First-Order Diffraction Tomography," Slaney et al, IEEE Transactions on Microwave Theory and Techniques, Vol. MTT 32, 1984, at pages 860–874 and in "Distortion In Diffraction Tomography Caused By Multiple Scattering," Azimi et al, IEEE Transactions on Medical Imaging, Vol. MI-2, No. 4, December 1983, at pages 176–195, or have used stationary planar arrays, as described in "A Microwave Diffraction Tomography System for Biomedical Applications," Peronnet et al, Proceedings of the 13th European Microwave Conference, September, 1983, pages 529–533, and in "Three-D Holographic Device Images RF Data Collected Once Over Entire Body," Pearce et al, RNM Images, April 1984, pages 32–33, 37 for acquiring the measured values from the transmitted radiation. In the systems described in the first three of the above articles, planar waves must be employed for irradiating the object. The images produced with these known systems are tomographs. In the system described in the last of the above articles, however, three-dimensional representations are attempted. In the systems in all of the articles, however, image reconstruction is undertaken with the assumption that the scattered field is generated by single scattering in the object being examined.

The four imaging systems described in the above-cited articles can therefore be employed only to a limited degree for medical diagnostic purposes, because those systems generate significantly falsified images of the $\epsilon$ distribution in biological tissue. One reason for this is that the assumption of single scattering (corresponding to the first Born approximation for the electromagnetic wave equation) is valid only for weakly scattering objects which are substantially homogeneous, and even under such conditions this assumption is only approximate. As is well known from the literature, both requirements (weak scattering and substantial homogeneity) are not characteristics of biological tissue.

The aforementioned articles in RNM Images discloses a measuring system wherein a plurality of individual detectors are arranged on a cylinder. These individual detectors are connected to a processing system for processing the measured data. Such a system requires a large number of individual detectors, and thus a corresponding number of processing channels, and is thus relatively complicated.

A holographic measuring system for radio-frequency is described in U.S. Pat. No. 3,887,923 wherein a plurality of antennas or individual detectors are also utilized. In this system, however, stationary antennas are again used. The system described therein is thus restricted to a linear array.

A method for recording acoustic, synthetic or microwave holograms is described in U.S. Pat. No. 3,818,427. In this method, a transmitter disposed in a container emits radiation in the direction of an object also in the container, and the resulting signal is sensed at the surface of liquid contained within the container. Sensing is undertaken by an individual (discrete) antenna. No three dimensional representation is possible with this method.

SUMMARY OF THE INVENTION

It is an object of the present invention to provide a method and apparatus for identifying the distribution of dielectric constants in an object which is not restricted to representing a tomograph single slice of the object, but rather permits calculation of the three-dimensional distribution of the dielectric constants of the object.

A further object of the present invention is to provide such a method and apparatus which achieves these results with a relatively low number of individual detectors and a minimum of processing channels.

Another object is to provide such a method and apparatus for generating images from any desired portion of the object.

Another object is to provide a method and apparatus which allows the three-dimensional distribution of the complex dielectric constants in the human body to be identified.

A further object of the present invention is to provide a method and apparatus which take multiple scattering of radiation in the object into consideration so that objects strongly scattering can be accurately represented.

The above objects are achieved in accordance with the principles of the present invention by a method and apparatus wherein the transmitted and scattered radiation is acquired in terms of amplitude and phase in a prescribed volume, and wherein the distribution of the dielectric constants in the object is calculated from the acquired signals in three-dimensional form, with the result of the calculations being forwarded for image presentation in selectable sections or slices through the object.

In contrast to the prior art, the method and apparatus disclosed herein make use of a three-dimensional volume within which measurements are undertaken, the incident radiation being measured within this volume by a microwave detector. The spatial distribution of the dielectric constants in the object can then be determined by calculation based on the data derived from the output signal of the microwave detector. Because the radiation is acquired in the prescribed volume, imaging can be undertaken with a relatively low number of detector elements within the microwave detector, in comparison to known cylindrical arrangements of detector elements. By means of mathematical operations which are known, for example from CT techniques or MR techniques, an arbitrary section or slice can be selected from the three-dimensional distribution. This section or slice can then be forwarded for representation on an image display means.

In a first embodiment of the method the detector is a detector array which is linearly displaceable. The detector array need not be flat, but can have an arbitrary shape.

In a second embodiment, the detector is is rotatable around the object. The detector array can be curved plane or flat plane or may, for example, be in the shape of a hemispherical shell or a segment of a cylinder. The radius of curvature of the detector array, however, should not be equal to the radius of the path of movement around the object.

In a further embodiment the detector is a line detector, and is mounted so as to be rotatable around the object as well as displaceable in a direction toward and away from the object.

In another embodiment, the detector may be an individual or discrete detector element which senses the selected volume with respect to amplitude and phase.

In a preferred embodiment, image reconstruction in accordance with the method disclosed herein is implemented taking multiple scattering into consideration. Because amplitude and phase of the scattered wave field are measured, the image reconstruction is of a holographic nature, analogous to optics. Mathematical operations which are particularly suited for this purpose are disclosed herein. Because the multiple scattering is taken into consideration for image generation, the $\epsilon$ distribution in the object can be precisely identified, as simulated calculations have confirmed. It is thus possible to use the method to particular advantage for medical diagnostics.

In an apparatus for implementing the above method, the microwave detector is arranged for acquiring transmitted an scattered radiation in the selected volume based on amplitude and phase, and the output signal of the detector is supplied to a computer which calculates the three-dimensional distribution therefrom.

The microwave detector in the apparatus may be as described above, i.e., a planar detector with means for linearly moving the detector toward and away from the object. The individual detectors or elements of the array can be arranged on a flat surface, and as is known from radar technology, the detectors may be in the form of dipole antennas.

DESCRIPTION OF THE PREFERRED EMBODIMENTS

Figure 1:
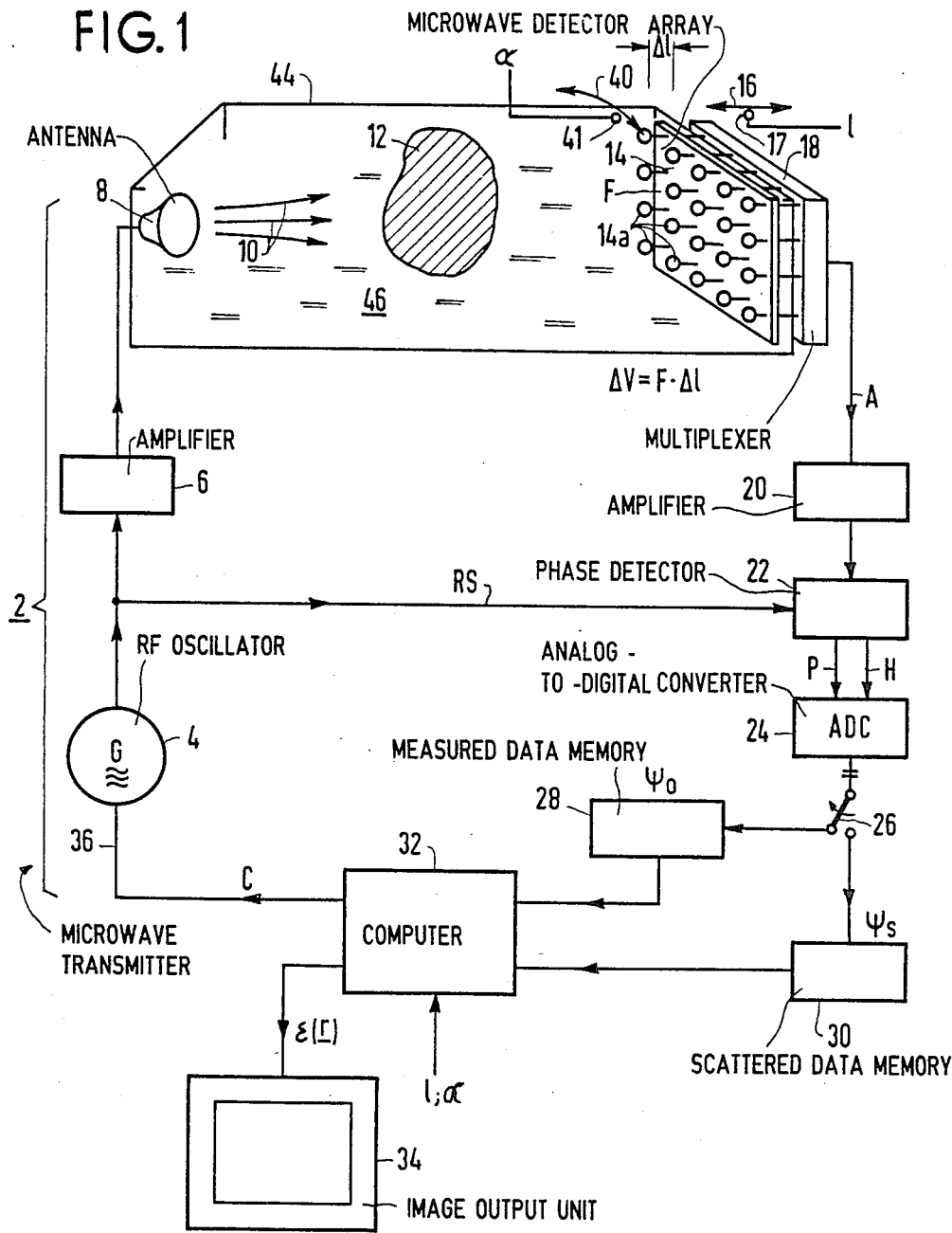
FIG. 1 is a schematic representation of an apparatus for identifying the distribution of the dielectric constants in an object constructed in accordance with the principles of the present invention and for implementing the method disclosed herein.

The apparatus shown in the drawing employs microwaves for identifying the distribution of the dielectric constants in an object, however, it will be understood by those skilled in the art that the apparatus shown in the drawing can also be employed using an ultrasonic radiator. The modifications required for this purpose are described in greater detail below.

The apparatus includes a microwave transmitter 2 which includes an RF-oscillator 4, an amplifier 6, and a transmission antenna 8 which is rotatable around an object 12. The transmitter 2 generates microwave radiation either pulsed or continuously. The waves emitted by the transmission antenna 8 need not be planar waves; the waves can form an arbitrary wave field. For reasons of wavelength-limited resolution and penetration depth, a radio-frequency f of a few gigahertz is suitable. It is possible to employ a plurality of transmission antennas 8 connected to the amplifier 6.

In a measuring mode, radiation 10 emitted by the microwave transmitter 2 is incident on the object 12 to be examined, and enters into interaction therewith. The radiation transmitted and scattered by the object 12 is incident on a microwave detector array 14. The array 14 includes a plurality of individual detectors or microwave reception antennas 14a, which are preferably arranged on a flat surface F. The microwave detector array 14 is linearly displaceable in the direction of maximum radiation propagation by means of an apparatus not shown in greater detail. The linear displacement of the array 14 is schematically indicated by the double arrow 16. The position 1 of the array 14 is identified with a position detector 17, the position preferably being identified in a non-contacting manner. Upon displacement along a path $\Delta 1$, the microwave detector array 14 moves through a prescribed volume $\Delta V = F \cdot \Delta 1$. The individual detector 14a of the array 14 are capable of emitting output signals which characterize the incident electromagnetic radiation field at the location of each individual detector 14a in terms of amplitude and time. The output signals of the detectors 14a of the array 14 are successively sampled with a multiplexer 18, which may also include a pre-amplifier. An output signal A formed in this manner is supplied to an amplifier 20.

It is also possible for each detector 14a of the array 14 to have its own amplifier allocated thereto. The circuit outlay, however, is increased in such an embodiment.

The amplified output signal A is compared to a reference signal RS in a phase detector 22. The reference signal RS is derived from the RF oscillator 4. The result of the comparison identifies the amplitude and relative phase of the signal A with respect to the RF oscillator output signal. These quantities are indicated by two output signals P (for phase) and H (for amplitude). The two output signals P and H are supplied to an analog-to-digital converter 24. The signals are converted therein to corresponding digital signals. The output signals of the converter 24 are supplied via a switch 26 to either a memory 28 for measured calibration data $\psi_o$ or to a data memory 30 for scatter field data $\psi_s$. In principle, a single data memory having a higher memory content alternately connected to follow the output of the converter 24. The data acquired in a calibration mode, without the presence of the object 12, are stored in the first memory 28, whereas the data which are acquired during an actual examination mode are stored in the second data memory 30. The outputs of the two memories 28 and 30 are supplied to a computer 32. The data from the two memories 28 and 30 are combined with each other in the computer 32, as described in greater detail below. The respective position 1 of the array 14 is thereby taken into consideration. The computer 32 identifies the three-dimensional distribution of the dielectric constants $\epsilon$ in the examined object 12. The output of the computer 32 is supplied to an image display unit 34 or to some other recording device. A section through the three-dimensional distribution can be selected (by hardware or software) at an input (not shown) of the computer 32, in a manner similar to that employed in computer tomography. A two-dimensional slice through the object 12 is thus shown in the image display unit 34. Based on need or interest, some other slice presentation can be selected. Three-dimensional presentations are also possible, wherein the viewing direction can be selected.

The computer 32 forms a control signal C for operating the RF oscillator 4. This control signal C is supplied to the RF oscillator 4 via a line 36.

As stated above, the microwave detector array 14 documents the radiation transmitted and scattered by the object 12. The individual detectors 14a of the detector array 14 can be arranged on a flat, cylindrical or spherical surface. In the embodiment shown in the drawing, a flat surface F is used. The displacement of the array 14 within the path $\Delta 1$ along the direction of maximum radiation propagation is undertaken in small steps. One set of data (amplitude and phase) for the location of each detector element 14a is identified in each step. In order to achieve an optimum resolution, the detector array 14 should cover a solid angle which is as large as possible.

It is also possible to move the detector array 14 around the object 12. This is also preferably undertaken in steps along a circular orbit or path, schematically indicated by the double arrow 40. In this embodiment, an image can be generated with relatively few individual elements 14a. Linear mobility and rotational mobility of the detector array 14 can be simultaneously provided. A data set (amplitude and phase) for the location of each detector element 14a is registered for every linear step at each rotational angle. An angular position detector 41 identifies the rotational angle position $\alpha$. The computer 32 is supplied with the output of the detector 41 so as to be informed of the angle position $\alpha$.

The detector array 14, in combination with the phase detector 22, is thus capable of measuring both the amplitude H and the phase P of the scattered field relative to the fixed reference signal RS. The use of an antenna array, i.e., a hard-wired antenna arrangement on a surface, is important to achieve a short data acquisition time and for high accuracy. The required accuracy and measuring time cannot be adequately achieved with a standard individual antenna in a scan mode, primarily for mechanical reasons.

In operating the apparatus shown in the drawing, as stated above, a calibration measurement without the object 12 is first undertaken, and the actual measurement of the object 12 is then executed. In the calibration mode, microwave radiation directed at the region wherein the object 12 will be located is first acquired in terms of amplitude and phase and is stored in the first memory 28. The detector array 14 employed for the calibration measurement is also used for the actual measurement. An array of detectors geometrically fashioned in some other manner could, however, also be employed. In the calibration mode, the detector array 14 is disposed at the location where the object 12 is to be located.

As described above, the calibration data are supplied to the first memory 28 (or to a common memory) after analog-to-digital conversion. In the actual measurement, the data are subsequently supplied to the second data memory 30. Preferably with the assistance of the reconstruction algorithm described below, the computer 32 generates the desired three-dimensional spatial distribution of the complex dielectric constants from both groups of measured data. This three-dimensional distribution can then be shown on the output unit 34.

The transmission antenna 8, the object 12, and the detector array 14 are disposed within a container 44 which is filled with a coupling medium 46 having a high dielectric constant. The coupling medium 44 may, for example, be alcohol, or oil, rubber or water, preferably water having $\epsilon = 80$. This achieves a favorable coupling of the microwave energy to the object 12, and further provides optimal wavelength contraction in comparison to the vacuum wavelength of the microwave radiation employed.

The mathematical basis for the image reconstruction employed herein is the non-homogeneous (scalar) Helmholtz equation. The exact solution to this equation is the Lippmann Schwinger integral equation:

$$\psi(r) = \psi_o(r) + \int G(r,r') V(r') \psi(r') d^3 r' \quad (1),$$

whereby $\psi_o$ is the incoming wave field, G is the Green's function of the Helmholtz equation and V(r') is the scattering potential. V(r') is defined by the dielectric properties of the object 12 and of the surrounding coupling medium 46 by the following relationship:

$$V(r) = \frac{\omega}{c} (\sqrt{\epsilon \mu} - \sqrt{\epsilon(r)\mu(r)}) \quad (2)$$

wherein $\epsilon$ is the dielectric constant of the surrounding homogeneous coupling medium 46 and $\epsilon(r)$ is the corresponding $\epsilon$ distribution in the object 12, $\omega$ is the radian frequency $2\pi f$, with f being the frequency of the microwave radiation.

In the biological field, the permeability $\mu$ is roughly $\mu = (r) = 1$. The speed of light is referenced c.

The goal of the imaging method is to identify $\epsilon(r)$ from the measured wave field $\psi(r)$. An approximate solution to equation (1) is the first Born approximation which is obtained by replacing the field $\psi$ in the integral by the undisturbed incoming field $\psi_o$. As already discussed above, this approximation is inadequate for medical diagnostic purposes.

A complete solution to equation (1) is possible because the object 12, and thus the scattering potential V(r), is finite, that is, V(r)=0 for $|r| > R$, where R is the radius of a sphere which completely surrounds the object 12 without including the individual detectors 14a. Equation (1) can be then separated into two equations (3a) and (3b), one equation for the observed scattered field $\psi_S = \psi - \psi_o$ and one equation for the internal field $\psi_{int}$ in the region of the object 12 ($|r| < R$) as follows:

$$\psi_S = G_S V \psi_{int} \quad (3a)$$

$$\psi_{int} = \psi_o + G_T V \psi_{int} \quad (3b).$$

This abbreviated notation corresponds to the operator formalism which is standard in quantum mechanics, i.e., the quantities may, but need not, be matrices. The solution to equations (3a) and (3b) is as follows:

$$V = G_S^{-1} \psi_S (\psi_o + G_T G_S^{-1} \psi_S)^{-1} \quad (4)$$

is the unit operator (i.e., the unit matrix given matrix calculation) and $G_S^{-1}$ is the inverted Green's function.

Thus, when the scattered field $\psi_S$ and the undisturbed incoming field $\psi_o$ are measured, $V(r)$ can be calculated by the computer 32. Subsequently, after conversion of equation (2), the dielectric constant distribution $\epsilon(r)$ can be calculated by the computer 32. The parameters (spacing, wave number, etc.) needed for the calculation of the Green's functions $G_S$ and $G_T$ are defined by the transmitter and detector arrangement and by the frequency f.

Matrix calculation is preferably employed.

Two types of representations can be employed for calculating the $\epsilon$ distribution by means of equations (2) and (4), as described below.

1. R Space Representation

In this case, the Green's functions $G_S$ and $G_T$ are non-diagonal, and the numerical calculation of V according to equation (4) requires inversion of the corresponding matrices. For a large number of measured values, i.e., given low resolution with large objects, and given high resolution with small objects, this calculation method is not appropriate because matrix inversion currently requires long calculation times and high memory capacities.

2. Fourier Representation

The other calculation method for V according to equation (4) is obtained by three-dimensional Fourier transformation of the quantities in equations (3a) and (3b). Because every Green's operator $G_T$ and $G_S$ is diagonal in Fourier space, matrix inversion can be avoided, i.e., the term $G^{-1}$ in equation (4) requires only a division by the corresponding Fourier component of $G_S$ or $G_T$. The use of FFT (FAST FOURIER TRANSFORMATION) techniques results in comparatively short calculation times, even given a high number of measured values. A type of real time representation is thus possible with the Fourier technique. This second calculation method is therefore preferred for use in the computer 32.

For the use of FFT techniques, it is necessary either to measure the scattered field with the detector array 14 in the three-dimensional Cartesian volume, which is scanned by displacement in the direction of the double arrow 16, or to recalculate measured values acquired in some other manner (not shown) onto a three-dimensional Cartesian grid by making use of interpolations.

Figure 2:
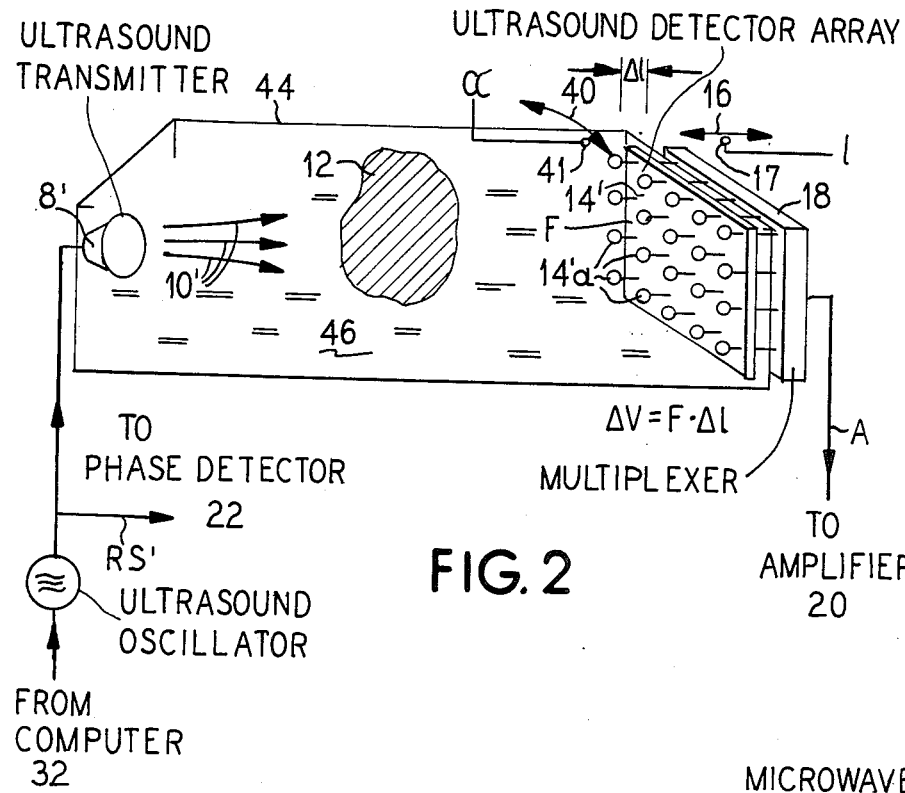
FIG. 2 is a schematic representation of a further embodiment of an apparatus for identifying the distribution of the dielectric constant in an object constructed in accordance with the principles of the present invention using ultrasound techniques.
Figure 3:
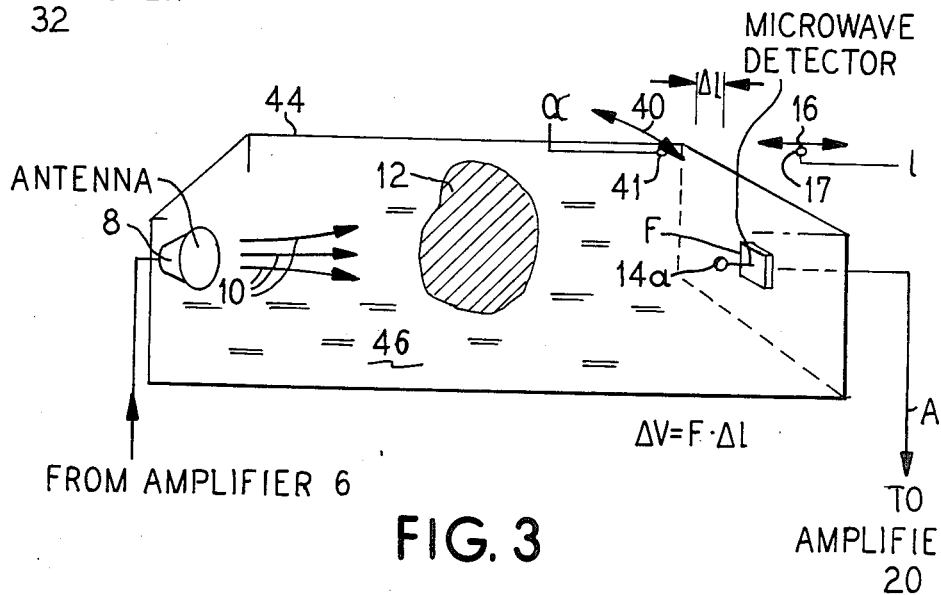
FIG. 3 is a schematic representation of an apparatus for identifying the distribution of the dielectric constant in an object constructed in accordance with the principles of the present invention using a single detector element.

In ultrasound tomography and ultrasound holography as well, noticeable inhomogenities of the speed of sound in tissue result in reduced image quality. Ultrasound propagation can also be described to a good approximation by the scalar Helmholtz equation. Particularly using the Fourier method, the reconstruction algorithm according to equations (2) and (4) can therefore also be applied for ultrasound imaging. In other words, the principle of the measuring apparatus shown in the drawing can be transferred to the field of ultrasound techniques. The illustrated apparatus can then serve for measuring the distribution of the speed of sound in the object 12 (instead of measuring the distribution of the dielectric constants), making use of the inventive concept disclosed herein. For ultrasound application, as shown in FIG. 2 the microwave transmitter to an ultrasound transmitter 8' which emits ultrasound radiation 10', the microwave detector array to an ultrasound detector array 14' consisting of a plurality of individual ultrasound detectors 14a', and the coupling medium having a high dielectric constant corresponds to an ultrasound coupling medium. As shown in FIG. 3, a single detector element 14a may be used in place of the array.

Although modifications and changes may be suggested by those skilled in the art it is the intention of the inventors to embody within the patent warranted hereon all changes and modifications as reasonably and properly come within the scope of their contribution to the art.

We claim as our invention:

1. A method for identifying the distribution of dielectric constants in an object in a scan of said object comprising the steps of:
    during said scan, emitting radiation directed at said object thereby causing said object to multiply scatter and transmit radiation attenuated by said object forming a three-dimensional attenuated and scattered radiation field;
    defining a selected volume outside said object in said attenuated and scattered radiation field;
    receiving said attenuated and scattered radiation within said selected volume;
    measuring at each of a plurality of selected locations within said volume the received radiation in terms of amplitude and phase to obtain a data set for said scan;
    calculating a three-dimensional distribution of the dielectric constants in said object from the amplitudes and phases of the radiation received within said selected volume in said data set based at least in part on the multiple scattering of said radiation within said object;
    selecting a section of said three-dimensional distribution; and
    visually displaying said section.

2. A method as claimed in claim 1, wherein the step of emitting radiation is further defined by emitting microwave radiation directed at said object.

3. A method as claimed in claim 1, wherein the step of emitting radiation is further defined by emitting ultrasonic radiation directed at said object.

4. A method as claimed in claim 1, wherein said radiation is received by a two-dimensional detector array, and comprising the additional step of linearly displacing said detector array in a direction toward and away from said object to receive said radiation within said selected volume.

5. A method as claimed in claim 4, comprising the additional step of rotating said array around said object.

6. A method as claimed in claim 1, comprising the additional steps of:
    undertaking a calibration measurement in the absence of said object with a radiation detector disposed at a position to be subsequently occupied by said object;

storing the measurements of phase and amplitude of said radiation in a memory from said calibration step; and using the stored calibration measurements in said calculating step.

7. A method as claimed in claim 1, wherein the step of calculating a three-dimensional distribution of the dielectric constants is further defined by calculating said distribution using the following equations:

$$V(r) = \frac{\omega}{c}(\sqrt{\epsilon\mu} - \sqrt{\epsilon(r)\cdot\mu(r)}) \text{ and}$$

$$V = G_S^{-1}\psi_S(1\psi_o + G_T G_S^{-1}\psi_S)^{-1},$$

wherein $V(r)$ is the scattering potential, $\omega = 2\pi$ f is the angular frequency of the emitted radiation, c is the speed of light, $\epsilon$ is the dielectric constant of the radiation coupling medium surrounding said object, $\mu$ is the permeability of said coupling medium, $\mu(r)$ is the permeability of said object, $G_S$ is the Green's function describing the propagation of the radiation from said object to a measuring location within said selected volume, $G_T$ is the Green's function describing the propagation of radiation between two locations in said object, $G_S^{-1}$ is the inverted Green's function $G_S$, $\psi_o$ is the incoming radiation field at the location of the object, $\psi_S$ is the scattered field at said measuring location, $\mathbf{1}$ is a unit operator, and $\epsilon(r)$ is said distribution of the dielectric constants in said object.

8. A method as claimed in claim 7, wherein the step of calculating is undertaken in a matrix format using fast Fourier transform techniques applied to the scattered field within said selected volume, and wherein $\mathbf{1}$ is the unit matrix.

9. A method as claimed in claim 1, wherein said radiation is received by a one-dimensional detector, and comprising the additional steps of:

linearly displacing said detector; and rotating said detector around said object.

10. An apparatus for identifying the distribution of dielectric constants in an object in a scan of said object comprising:

means for emitting radiation directed at said object during said scan thereby causing said object to multiply scatter and transmit radiation attenuated by said object forming a three-dimensional attenuated and scattered radiation field;

means for defining a selected volume outside of said object in said attenuated and scattered radiation field;

means for receiving said attenuated and scattered radiation within said selected volume;

means for measuring at each of a plurality of selected locations within said volume the received radiation in terms of amplitude and phase to obtain a data set for said scan;

means for calculating a three-dimensional distribution of the dielectric constants in said object from the amplitudes and phases of the radiation received within said selected volume in said data set based at least in part on the multiple scattering of said radiation within said object;

means for selecting a section of said three-dimensional distribution; and means for visually displaying said section.

11. An apparatus as claimed in claim 10, wherein said means for emitting is a microwave transmitter.

12. An apparatus as claimed in claim 10, wherein said means for emitting is an ultrasonic transmitter.

13. An apparatus as claimed in claim 10, wherein said means for receiving radiation is a detector array having a plurality of individual detector elements.

14. An apparatus as claimed in claim 13, wherein said individual detector elements of said array are disposed on a flat surface.

15. An apparatus as claimed in claim 13, wherein said individual detector elements are dipole antennas.

16. An apparatus as claimed in claim 10, wherein said means for receiving radiation is a two-dimensional detector array, further comprising:

means for moving said means for receiving radiation linearly toward and away from said object through said selected volume.

17. An apparatus as claimed in claim 10, further comprising means for rotating said means for receiving radiation around said object.

18. An apparatus as claimed in claim 10, further comprising a container in which said means for emitting radiation, said means for receiving radiation, and said object are disposed, said container being filled with a coupling medium having a high dielectric constant.

19. An apparatus as claimed in claim 10, wherein said means for emitting radiation includes an RF oscillator and wherein said means for measuring the received radiation includes a phase sensitive detector, and wherein said phase sensitive detector has an input connected to an output of said RF oscillator for supplying the output of the RF oscillator to the phase sensitive detector as a reference signal.

20. An apparatus as claimed in claim 19, further comprising an analog-to-digital converter connected to an output of said phase sensitive detector, and a means for storing data having an input connected to the output of said analog-to-digital converter.

21. An apparatus as claimed in claim 20, wherein said means for storing said data comprises a first memory for storing calibration data taken in the absence of said object with said means for receiving radiation disposed at a position subsequently to be occupied by said object, and a second memory for storing measured data from said object, and means for switching the output of said analog-to-digital converter to one of said first or second memories.

22. An apparatus as claimed in claim 21, wherein said means for calculating is a computer having inputs respectively connected to outputs of said first and second memories, and having an output connected to said means for visually displaying said section.

23. An apparatus as claimed in claim 22, further comprising a control line from said computer to said means for emitting radiation for controlling operation thereof.

* * * * *